US005514712A

United States Patent [19]

LeClere

[11] Patent Number: 5,514,712
[45] Date of Patent: May 7, 1996

[54] USE OF OILS OF CHAULMOOGRA IN THE COSMETIC AND PHARMACEUTICAL DOMAIN, PARTICULARLY IN DERMATOLOGY, FOR HARMONIZING PIGMENTATION OF THE SKIN

[75] Inventor: Jacques LeClere, Noisiel, France

[73] Assignee: Shiseido International France, Paris, France

[21] Appl. No.: 259,493

[22] Filed: Jun. 14, 1994

[30] Foreign Application Priority Data

Jun. 15, 1993 [FR] France ............................ 93 07168

[51] Int. Cl.$^6$ ..................... A61K 31/215; A61K 31/195
[52] U.S. Cl. .................... 514/530; 514/559; 514/560
[58] Field of Search ..................... 514/530, 559, 514/560; 424/195.1, 59; 554/222

[56] References Cited

U.S. PATENT DOCUMENTS

| | | | |
|---|---|---|---|
| 3,882,238 | 5/1975 | Quackenbush et al. | 424/303 |
| 3,918,983 | 11/1975 | Papalos . | |
| 3,983,228 | 9/1976 | Woodhour et al. . | |
| 4,075,318 | 2/1978 | Kelly et al. | 424/70 |
| 4,294,852 | 10/1981 | Wildnauer et al. | 424/317 |
| 4,386,067 | 5/1983 | Guillon . | |
| 4,393,043 | 7/1983 | Koulbanis et al. . | |
| 4,740,432 | 4/1988 | Bosserelle . | |
| 4,859,668 | 8/1989 | Noga et al. | 514/231.2 |
| 4,950,688 | 8/1990 | Bowser et al. | 514/47 |
| 4,985,255 | 1/1991 | Higa et al. | 424/847 |
| 5,061,480 | 10/1991 | Marchese et al. | 425/59 |
| 5,175,190 | 12/1992 | Burton et al. | 514/560 |
| 5,279,817 | 1/1994 | Franco . | |
| 5,308,609 | 5/1994 | Etheredge, III | 424/61 |
| 5,319,117 | 6/1994 | Fabry et al. . | |
| 5,328,691 | 7/1994 | Horrobin et al. | 424/401 |
| 5,342,965 | 8/1994 | Behr et al. . | |
| 5,352,440 | 10/1994 | Gilchest et al. | 424/59 |

FOREIGN PATENT DOCUMENTS

| | | |
|---|---|---|
| 0570171 | 8/1961 | Belgium . |
| 0002049 | 12/1964 | France . |
| 2518402 | 6/1983 | France . |

OTHER PUBLICATIONS

Stedman's Medical Dictionary, 25th Edition p. 1270, (1990).
WPIDS No. 83-718566, Abstract of FR2518402, "Cosmetic compsn. contg. Chaulmoogra oil . . . ", (1993).
WPIDS No. 76-85951X, Abstract of JP51110540A, "Novel Chaulmoogri and amides prepn . . . ", (1993).
Chem. Abs. No. 79:64794 of J. Sci. Food Agr. (1973), 24(6) 669–74, Senguta et al.

Primary Examiner—Richard L. Raymond
Assistant Examiner—Deborah Lambkin
Attorney, Agent, or Firm—Ladas & Parry

[57] ABSTRACT

The present invention relates to the use of oils of chaulmoogra and derivatives thereof, particularly in the form of esters or salts, for preparing a cosmetic or pharmaceutical, particularly dermatological composition, intended for harmonizing the pigmentation of the skin. It concerns in particular a process for harmonizing tanning.

5 Claims, No Drawings

USE OF OILS OF CHAULMOOGRA IN THE COSMETIC AND PHARMACEUTICAL DOMAIN, PARTICULARLY IN DERMATOLOGY, FOR HARMONIZING PIGMENTATION OF THE SKIN

FIELD OF THE INVENTION

The present invention relates to a novel use of oils of chaulmoogra in the cosmetic and pharmaceutical domain, particularly in dermatology, for harmonizing pigmentation of the skin.

BACKGROUND OF THE INVENTION

At the present time, in cosmetology, the principal vocation of sun-products is the more or less high protection of the skin from UVA-UVB radiations. Such protection is due to the presence of filters which, depending on their chemical structure, reflect or absorb the solar radiations in a more or less broad zone of the spectrum.

Although these cosmetic products thus ensure a slow, progressive tanning, they do not respond to one preoccupation of the user, that of the harmonization of the pigmentation, the homogeneous distribution of the melanin, in order to prevent the appearance of slightly less pigmented marks after exposure.

Furthermore, in medicine, a very large number of diseases, translated by a localized deficiency of the pigmentation, are known. Such disorders are characterized by a reduction, even disappearance, of the epidermic and/or follicular melanocytes. Such hypo- or amelanoses are localized and affect only certain regions of the skin.

By way of example, this is the case of vitiligo, a disorder affecting about 1% of the population in Europe. It is translated by achromic marks disseminated at preferential sites (rear face of the elbows, front face of the knees, periphery of the lips or zone of friction).

These marks are due to the absence of melanic pigment at the level of the basal layer of the epiderm. Three etiological hypotheses are put forward to explain the disappearance of the melanocytes: genetic factors (30% of the cases), immunological factors (associated with auto-immune disorders) or nervous factors (psychological shock, stress).

Other types of hypomelanoses may appear further to external aggressions of physical type (heat burns) or chemical type (phenol, local corticoids, etc . . . ) or mycosis (pytiriasis versicolor).

At the present time, oral photochemotherapy may be considered as the only therapeutics for vitiligo: absorption of 8-methoxypsoralene or 5-methoxypsoralene. However, the risk of phototoxicity is great.

In local treatment, dermocorticoids of type II–III are used in certain precise cases. Surgical techniques such as autologous autografts from punch biopsies, grafts of blister roofs or of melanocytes are presently evoked and proposed in rare cases, but often remain at the experimental stage.

Oils of chaulmoogra are extracted from seeds of various species of the Flacourtiaceae family, ligneous tropical plants of asiatic (India, Burma, Vietnam, Philippines), African (Central Africa) and American (Brazil) origin.

Chaulmoogra seeds contain little water, 4 to 6% of mineral matter, 15 to 20% proteins.

The proportion of lipids varies depending on the species, but is always high: 30 to 50%.

Chaulmoogra oils contain 1 to 3% unsaponifiable matter (sterols, carotenoids), unsaturated fatty acid glycerides comprising a pentene cycle attached to a linear side chain terminated by a carboxylic function.

The three principal acids of this type are:

chaulmoogric acid, abundant in the African species (60 to 80%) responding to formula:

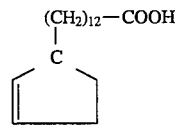

hydnocarpic acid, abundant in the Asiatic species (50 to 70%), responding to formula:

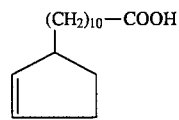

gorlic acid, always present but in small quantities (8 to 15%), responding to formula:

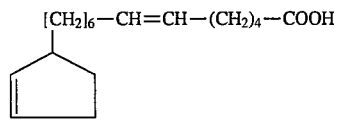

10 to 12% of fatty acid of palmitic, oleic, myristic, stearic and palmitoleic type are also found in these oils.

The principal sources of oil are the following varieties:

*taraktogenos kurzii*
*hydnocarpus wightiana*
*hydnocarpus heterophylla*
*hydnocarpus anthelmintica*
*hydnocarpus alpina*
*hydnocarpus cauliflora*
*hydnocarpus dawnensis*
*hydnocarpus hutchinsonii*
*hydnocarpus ovoidea*
*hydnocarpus subfalcata*
*hydnocarpus venenata*
*hynocarpus verrucosa*
*hydnocarpus woodii*
*oconba echinata* whose butter is called Gorli butter
*caloncoba welwitschii*
*carpotroche brasiliensis*
*asteriastigma macrocarpa*
*mayna odorata*
*lindakeria denrata*
*caloncoba glauca*

These oils have traditionally been used in the treatment of leprosy by the internal, external and parenteral route.

By the topical route, they have proved effective in the first stages of the disease by causing the size of the nodules to regress.

It appears that their activity is essentially due to the three principal acids mentioned, of which the spatial structures are close to the cyclopentanoperhydrophenanthrene ring, characteristic of the sterols. Ethyl, benzyl and methyl esters have been synthesized in order to improve acceptability and tolerance. Similarly, the salts obtained (sodium chaulmoograte, sodium hydnocarpate) exert a dissolving action on the lecithins and cholesterol, which would explain their action on the waxy envelope of the bacilli of leprosy and of tuberculosis.

However, since the arrival of sulfones, and rifampicine, their use in this domain has much regressed.

An anti-inflammatory power (reduction of the oedemas) and lipid-lowering power (reduction of cholesterolaemia) have also been demonstrated.

More recently, French Patent No. 2 518 402 has described compositions for cosmetic use, containing oils of chaulmoogra, modified or not.

Such compositions are used for healing infectious sites or for regularizing the sebaceous activity.

Applicants have now quite surprizingly discovered that oils of chaulmoogra as well as their derivatives, in particular the salts and esters thereof, presented the property of pigmenting piebald (achromic) cutaneous zones by migration of the pigmentation from zones already pigmented, i.e. from the epidermic and/or follicular melanin, after repeated applications.

SUMMARY OF THE INVENTION

The present invention therefore relates to the use in cosmetology and dermatology of oils of chaulmoogra and derivatives thereof, as skin-pigmenting agent.

More precisely, in accordance with a first aspect, the invention concerns a novel use of oils of chaulmoogra and derivatives thereof, particularly their salts and esters, for preparing a cosmetic or pharmaceutical, particularly dermatological composition intended for harmonizing the pigmentation of the skin.

In order to prepare the cosmetic or pharmaceutical, and particularly dermatological compositions intended, according to the invention, to modify the pigmentation of the skin, all sorts of oils of chaulmoogra may be used, in particular oils extracted from the following varieties:

*taraktogenos kurzii*

*hydnocarpus wightiana*

*hydnocarpus heterophylla*

*hydnocarpus anthelmintica*

*hydnocarpus alpina*

*hydnocarpus cauliflora*

*hydnocarpus dawnensis*

*hydnocarpus hutchinsonii*

*hydnocarpus ovoidea*

*hydnocarpus subfalcata*

*hydnocarpus venenata*

*hydnocarpus verrucosa*

*hydnocarpus woodii*

*oconba echinata* whose butter is called Gorli butter

*caloncoba welwitschii*

*carpotroche brasiliensis*

*asteriastigma macrocarpa*

*mayna odorata*

*lindakeria dentata*

*caloncoba glauca*

These oils are extracted from the seeds by cold or hot pressing, by extraction by solvents or any other known process for extracting plant oils.

According to the present invention, it is preferred to resort to a process for extraction by solvent, particularly highly purified hexane. The process advantageously employs a step of lixiviation followed by an evaporation in vacuo of the solvent.

The acids contained in the oil may be free or salified in the form of salts, for example of sodium or potassium.

These oils may possibly be chemically modified in order to prepare esters, for example ethyl, methyl or benzyl esters or inter-esters of the fatty acids contained in the oil.

According to a particularly advantageous variant of the invention for obtaining a slow release, continuous in time, the acids contained in the oil may also be grafted, i.e. coupled, by a peptide bond, to a protein of animal or plant type. This allows a slow release, continuous in time (delay effect) under the action of the proteases, during application.

The cosmetic or pharmaceutical, particularly dermatological compositions useful according to the invention advantageously contain from 0.001 to 30% by weight of chaulmoogra oil or derivatives, preferably from 0.1 to 5% by weight.

The oil or its derivative may be introduced within the cosmetic or pharmaceutical composition by any means conventionally used in the domain, in particular aiming at emulsion thereof. It may also be encapsulated in all thermodynamically stable, galenic forms.

The following may be mentioned by way of examples: microcapsules (also called microspheres), hollow spheres limited by membranes of variable constitution (component of biological origin, for example) and of size included between some microns and some millimeters. Mention may also be made of mono- or plurilamellar liposomes: these are small hollow spheres whose membrane is constituted by one or more bilayers of lipidic molecules including the preparation to be encapsulated.

These oils may be used and incorporated in all dermatologically acceptable cosmetic preparations in the form of emulsion, gel, milk, mask and in free form or encapsulated and intended:

for face and body care, for example: day creams, night creams, beauty masks, foaming gels-oils, sun products, for care and protection of the hair and/or scalp, for example: shampoos, medicated creams, capillary lotions, for make-up products, for example foundation creams.

Oils of chaulmoogra or derivatives thereof may also be introduced in any pharmaceutically acceptable vehicle for preparing a composition for dermatological use.

By way of example, it may be question of vehicles of oil-in-water or water-in-oil emulsion type, of micro-emulsions, suspensions, micellar solutions, ointments, lotions, liniments, gels or hydrogels.

It has appeared that the cosmetic or pharmaceutical compositions described hereinabove and containing oils of chaulmoogra or derivatives thereof presented the quite surprizing property of activating, with or without sun, the melanocytes in the cutaneous zones treated and of considerably increasing their dendricity allowing a transfer of synthesized melanin to the adjacent keratinocytes.

This property was demonstrated in the tests described hereinafter:

1) Protocol of the test:

The study was made on 16 subjects. They were selected as presenting contiguous pigmented and non-pigmented zones of skin. They were divided into two batches.

Batch 0: 8 negative controls not receiving any treatment

Batch 1: 8 treated with pure oil.

Fifteen days before the first application, a tattoo is made 1 cm from the edge of the pigmented zone so as to have a visual mark.

After this period, the subjects undergo their first treatment:

daily application in the morning, 5 days out of 7 for eight consecutive weeks at the rate of 0.1 ml per subject.

Application is made at the level of the pigmented cutaneous zone extending beyond the piebald zone towards the tattoo by smooth massage with the aid of a fingerstall.

Cutaneous samplings the day of tattooing, a biopsy is made in all the subjects at the level of the pigmented zone. In the batch to be treated, the biopsy is made at a distance from the site retained to receive the product.

at the end of the test, four samples are again taken:
two on the pigmented zone,
two other samplings of which one on the pigmented zone having migrated and one on the piebald zone.

2) Examinations

2a) Visual examination:

Visual observation made it possible to assess the extension of the pigmented zone on the achromic zone.

Such migration of the pigmented zone was observed on all the subjects from the end of the fifth week of treatment. The advance was assessed between three and six millimeters for all the subjects.

2b) Histochemical reaction on biopsies:

It makes it possible to assess, quantitatively, modifications in the pigmentation. It is question of the reaction to L-Dopa on the separated epiderms after biopsies.

By observation under an optical microscope (magnifying power of 20), a clear accentuation is noted of the dendricity of the melanocytes at the end of treatment, as well as an increase in the quantity of melanin distributed in the epiderm.

No abnormal morphological modification was observed. The melanocyte count demonstrated the absence of increase in the melanocyte density.

2c) Observation with transmission electron microscope:

Ultrastructural observation revealed in the treated skins the presence of very active melanocytes with a hyperdendricity and a transfer of synthesized melanin to the adjacent keratinocytes.

A verification of the absence of inflammatory reaction was made by studying biopsies after staining with modified MASSON Trichrome.

The histological control/treated subject images were comparable and confirmed the absence of signs of inflammation.

A second study was made on 14 subjects in accordance with the same protocol as the previous study, but, after application of the oil, irradiating the treated zone.

Irradiations were effected 5 days out of 7 with the aid of PHILIPPS tubes ref. 40 W/12 emitting in the wavelength of between 280 and 340 nm.

The exposure time corresponded to half the minimum erythematous dose in order not to cause inflammatory reactions capable of causing the melanocytes to multiply.

Daily visual observation before each treatment made it possible to assess the extension of the pigmented zones on the achromic zones. At the level of the treated/irradiated site, migration was observed on all the subjects from the 3rd week, therefore 2 weeks earlier than the study previously carried out without irradiation.

Observations made with the optical and transmission electron microscopes proved to be identical to the previous study.

This property made it possible to envisage the use of these oils of chaulmoogra in all cosmetic or dermatological uses where it is desired to modify locally the pigmentation of the skin.

In fact, in order to obtain such an effect, it will suffice to apply a cosmetic or pharmaceutical composition containing an oil of chaulmoogra as described hereinabove on at least one more strongly pigmented zone adjacent a less strongly pigmented zone.

According to another of its aspects, the invention thus relates to a process for cosmetic treatment of the skin intended to pigment or modify its pigmentation, characterized in that it consists in applying a cosmetic composition containing from 0.001 to 30% by weight, preferably from 0.1 to 5% by weight of oil of chaulmoogra or a derivative thereof.

In order to obtain the desired effect of increasing the pigmentation of a hardly pigmented zone of skin adjacent a more pigmented or strongly pigmented zone, the cosmetic composition containing the oil of chaulmoogra is advantageously applied on at least a part of the more pigmented zone adjacent the zone whose pigmentation it is desired to increase.

By repeating such application, a progressive increase in the pigmentation of the less pigmented zone is observed.

This process proves particularly useful to obtain effects of harmonization of tanning when certain zones of the body are less intensely tanned than adjacent zones.

In accordance with another aspect, the invention also relates to a process for harmonizing tanning, consisting in applying a cosmetic composition containing 0.001 to 30% by weight, preferably 0.01 to 5% by weight of oil of chaulmoogra, or a derivative thereof, on at least a part of a tanned zone adjacent a non-tanned or less intensely tanned zone of which it is desired to increase tanning.

Repeated application of such a composition leads to an excellent uniformization of the tanning.

The invention also concerns a process for therapeutic treatment of confined hypomelanoses, consisting in applying in similar manner a pharmaceutical composition as described hereinabove on a pigmented zone adjacent a depigmented macula.

In this way, in dermatology, in the case of confined hypomelanoses, this process allows pigmentation of the apigmented zones by migration of the melanin present at the level of the peripheral edge of the depigmented maculas and/or hair follicles.

The following non-limiting examples are given purely to illustrate the invention.

EXAMPLES

The proportions given hereinbelow are expressed in percentages by weight.

EXAMPLE 1

Vehicle=oil-in-water emulsion

| | |
|---|---|
| . Sterile demineralized water | qsp 100.00% |
| . Carbopol 940 | 0.20% |
| . Triethanolamine | 0.25% |
| . Butylene glycol | 4.00% |
| . Glyceryl stearate | 3.00% |
| . Oil of chaulmoogra | 2.00% |
| . Myristil myristate | 2.50% |
| . Acetylated lanolin | 3.00% |
| . Stearate of PEG 20 | 3.00% |

-continued

|  |  |
|---|---|
| . Ketostearyl octanoate | 2.00% |
| . oil of paraffin | 1.00% |
| . Lanolin alcohol | 0.50% |
| . Octyl methoxycinnamate | 3.00% |
| . Kathon cg | 0.10% |
| . Allantoin | 0.10% |

EXAMPLE 2

Vehicle=hydrating gel

|  |  |
|---|---|
| . Demineralized water | qsp 100,00% |
| . Glyceryl polyacrylate | 3.00% |
| . Propylene glycol | 2.00% |
| . Dimethicone | 1.00% |
| . Phenoxyethanol | 0.60% |
| . Triethanolamine | 0.30% |
| . Carbopol 934 | 0.30% |
| . Hyaluronic acid | 0.50% |
| . Trisodium EDTA | 0.10% |
| . Methyl paraben | 0.30% |
| . Oil of chaulmoogra | 2.00% |
| . Benzophenone 3 | 3.00% |
| . Lauryl ether POE7 | 2.00% |
| . Isoparaffin | 1.00% |
| . Polyacrylamide | 2.00% |

What is claimed is:

1. A method for therapeutic treatment of confined hypomelanoses, comprising applying a pharmaceutical composition comprising from 0.001 to 30% by weight of oils of chaulmoogra said oils of chaulmoogra comprising unsaponifiable components, fatty acid glycerides and fatty acids wherein the fatty acids are free, esterified, salified, coupled by a peptide bond to a protein of animal or plant type or a mixture thereof, to a pigmented zone adjacent a depigmented macula.

2. The method according to claim 1, wherein said composition comprises from 0.1 to 5% by weight of oils of chaulmoogra.

3. A method for harmonizing pigmentation or tanning of skin by activating the melanocytes and increasing their dendricity, comprising applying to at least one more strongly pigmented or tanned zone adjacent a less strongly pigmented or tanned zone of the skin a composition comprising as an active ingredient oils of chaulmoogra said oils of chaulmoogra comprising unsaponifiable components, fatty acid glycerides and fatty acids wherein the fatty acids are free, esterified, salified, coupled by a peptide bond to a protein of animal or plant type, or a mixture thereof, said oils of chaulmoogra being present in an amount effective to harmonize the pigmentation or tanning of the skin.

4. A method according to claim 3, wherein said composition contains from 0.001 to 30% by weight of oils of chaulmoogra.

5. A method according to claim 3 wherein said composition contains from 0.1 to 5% by weight of oils of chaulmoogra.

* * * * *

UNITED STATES PATENT AND TRADEMARK OFFICE
CERTIFICATE OF CORRECTION

PATENT NO. : 5,514,712
DATED : May 7, 1996
INVENTOR(S) : Jacques Leclere

It is certified that error appears in the above-indentified patent and that said Letters Patent is hereby corrected as shown below:

On title page, item [75]

"LeClere" should be -- Leclere --.

Signed and Sealed this

Thirty-first Day of December, 1996

*Attest:*

BRUCE LEHMAN

*Attesting Officer*    *Commissioner of Patents and Trademarks*